United States Patent [19]

Gross

[11] Patent Number: Plant 6,592

[45] Date of Patent: Feb. 7, 1989

[54] POINSETTIA NAMED SUPJIBI

[76] Inventor: Eduard Gross, 16250 Blanzac, Nanteuillet, France

[21] Appl. No.: 32,831

[22] Filed: Apr. 1, 1987

[51] Int. Cl.[4] ..... A01H 5/00

[52] U.S. Cl. ..... Plt./86

[58] Field of Search ..... Plt./86

*Primary Examiner*—Robert E. Bagwill

*Attorney, Agent, or Firm*—Jordan and Hamburg

[57] ABSTRACT

A new poinsettia cultivar distinguished by large, bright red bracts, large, thick stems and leaves and a short growth habit is herein described. The stems of this plant are noticeably strong with short internodes, yet possessing a strong self-branching habit. As a flowering potted plant, it performs equally well as a single-stemmed, unpinched plant or as a branched, pinched plant.

1 Drawing Sheet

BACKGROUND OF THE NEW PLANT

This new poinsettia originated as a result of a cross breeding of my unpublished variety Mh×my variety Grotifer; the new variety was tested and was produced by me in my greenhouses in Nanteuillet, 16250 Blanzac (France).

I selected this plant because of its large bright red bracts, thick green leaves and thick red bracts, short growth habit, thick, strong stems and self-branching characteristics. This new variety flowers equally well as either a pinched, multiple branched plant or as an unpinched single stem plant. The plant's characteristics are unique. The plant is recognizable as being different from any other poinsettia variety. I propagated this new plant by vegetative cuttings through successive generations, which time and again has shown its thick stems and leaves, short stature and bright red bracts which have remained unchanged from generation to generation.

DESCRIPTION OF THE DRAWING

My new variety of poinsettia is illustrated by the accompanying full color photographic drawing, the colors being as true to that herein specified as is reasonably possible.

DESCRIPTION OF THE NEW PLANT

The following is a detailed description of this new poinsettia as observed under greenhouse culture at Nanteuillet, 16250 Blanzac (France). Color designations are according to The R.H.S. Colour Chart by The Royal Horticultural Society of London, England.

THE PLANT

Origin: Cross breeding of unpublished variety Mh×variety Grotifer.

Classification:

*Botanic.—Euphorbia pulcherrima.*

Form: Shrub.

Height: Short.

Growth habit:

*As a single stem.*—Upright, but short. Leaves and bracts are unusually thick and large. The stems are thick and strong with closely spaced nodes. I observed flowering stems of 25–30 cm length with red bract presentations 35–40 cm in diameter.

*As a branched plant.*—Upright with many stems producing a compact, bushy plant.

*Growth rate.*—Very fast. Rooting of vegetative cuttings occurs in 15 to 20 days under intermittent mist and the plant will flower in about 8 weeks under continuous long night conditions and night temperatures of 16 to 18 degrees C.

Foliage: This plant has unusually large, thick and erect dark green leaves, with the plane of the leaf blade nearly perpendicular to the stem. The larger leaves typically have leaf blades 15–16 cm long and 12–13 cm wide and leaf petioles 7–8 cm long.

*Leaf shape.*—Typical leaves are ovate with entire to weakly lobed margins.

*Color.*—Upper side — Near RHS 136A or 139A. Upper side — Between RHS 138A and 138B.

Bracts: Generally there are 12–14 uniformly colored bright red bracts, typically thicker and larger than most poinsettia cultivars. It is not unusual for the larger bract-leaf blades to be 17–18 cm long and 15–16 cm wide with short leaf petioles, 3–4 cm long. The short bract petioles result in a bract presentation with a close, tight center.

*Shape.*—The bracts are ovate with entire margins.

*Color.*—Upper side — Darker than RHS 45C and near RHS 45B. Under side — Near RHS 47B.

I claim:

1. A new and distinct poinsettia cultivar, substantially as herein shown and described, particularly distinguished by large, bright red bracts, large thick stems and leaves and a self-branching growth habit.

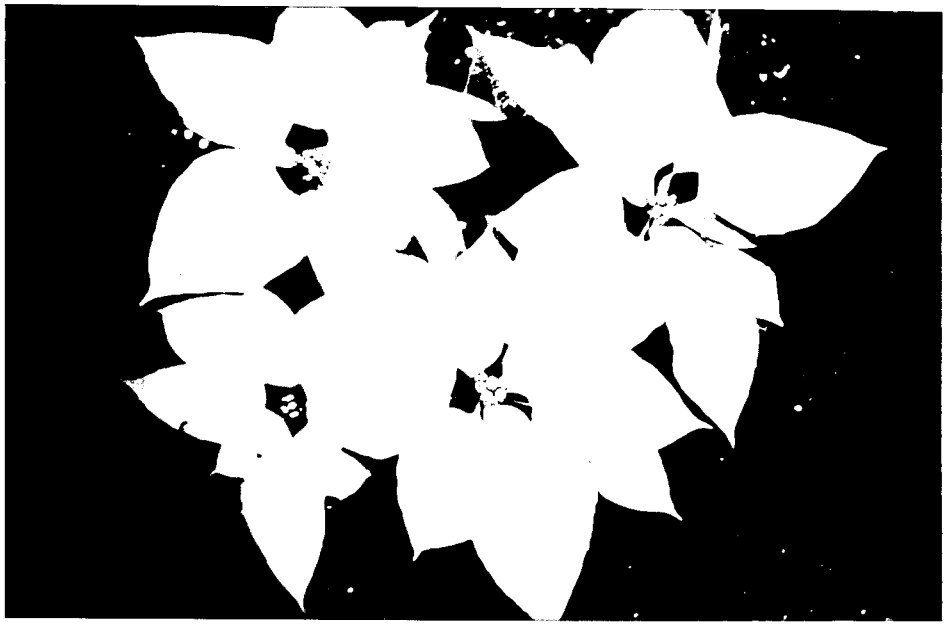

* * * * *